US009546917B2

(12) United States Patent
Groden et al.

(10) Patent No.: US 9,546,917 B2
(45) Date of Patent: Jan. 17, 2017

(54) STRAIN AMPLIFICATION SENSOR

(71) Applicant: THE REGENTS OF THE UNIVERSITY OF MICHIGAN, Ann Arbor, MI (US)

(72) Inventors: Mark D. Groden, Ann Arbor, MI (US); Matthew D. Collette, Ann Arbor, MI (US)

(73) Assignee: The Regents of The University Of Michigan, Ann Arbor, MI (US)

( * ) Notice: Subject to any disclaimer, the term of this patent is extended or adjusted under 35 U.S.C. 154(b) by 120 days.

(21) Appl. No.: 14/669,139

(22) Filed: Mar. 26, 2015

(65) Prior Publication Data

US 2015/0285694 A1 Oct. 8, 2015

Related U.S. Application Data

(60) Provisional application No. 62/063,449, filed on Oct. 14, 2014, provisional application No. 61/970,417, filed on Mar. 26, 2014.

(51) Int. Cl.
*G01B 7/16* (2006.01)
*G01L 1/00* (2006.01)
(Continued)

(52) U.S. Cl.
CPC .................. *G01L 1/04* (2013.01); *E21B 49/00* (2013.01); *G01B 5/30* (2013.01); *G01B 7/16* (2013.01);
(Continued)

(58) Field of Classification Search
CPC .......... G01B 5/30; G01B 7/16; G01M 5/0041; G01M 5/0025; G01L 1/10; G01L 1/20; G01L 1/22; G01L 1/2206; G01L 1/2287; G01L 5/106; G01N 2203/0016; E21B 49/00; H01C 17/00
(Continued)

(56) References Cited

U.S. PATENT DOCUMENTS 3,888,115 A 6/1975 Schwartz
5,423,224 A * 6/1995 Paine ....................... G01B 7/16
73/765
(Continued)

FOREIGN PATENT DOCUMENTS

JP 2013-245992 A 12/2013
WO 2009/103042 A2 8/2009
(Continued)

OTHER PUBLICATIONS

International Search Report and Written Opinion mailed Dec. 14, 2015 regarding PCT/US2015/022668.

*Primary Examiner* — Lisa Caputo
*Assistant Examiner* — Jonathan Dunlap
(74) *Attorney, Agent, or Firm* — Harness, Dickey & Pierce, PLC

(57) ABSTRACT

A strain amplification sensor having a first base portion being coupled to a first member to be strain measured, a second base portion being coupled to a second member to be strain measured, and an amplifying lever system pivotally coupled between the first base portion and the second base portion. The amplifying lever system includes attachment locations that induce opposing relative motion resulting in detectable deflection of the amplifying lever system in response to application of strain between the first base portion and the second base portion.

20 Claims, 4 Drawing Sheets

(51) Int. Cl.
| | |
|---|---|
| *G01L 1/04* | (2006.01) |
| *G01L 5/10* | (2006.01) |
| *G01M 5/00* | (2006.01) |
| *G01L 1/22* | (2006.01) |
| *G01L 1/10* | (2006.01) |
| *H01C 17/00* | (2006.01) |
| *E21B 49/00* | (2006.01) |
| *G01B 5/30* | (2006.01) |
| *G01L 1/20* | (2006.01) |

(52) U.S. Cl.
CPC .. *G01L 1/10* (2013.01); *G01L 1/20* (2013.01); *G01L 1/22* (2013.01); *G01L 1/2206* (2013.01); *G01L 1/2287* (2013.01); *G01L 5/106* (2013.01); *G01M 5/0025* (2013.01); *G01M 5/0041* (2013.01); *G01N 2203/0016* (2013.01); *H01C 17/00* (2013.01)

(58) Field of Classification Search
USPC .................................. 73/781–782, 790, 826
See application file for complete search history.

(56) References Cited

U.S. PATENT DOCUMENTS

| | | |
|---|---|---|
| 8,104,358 B1 | 1/2012 | Jia et al. |
| 9,382,960 B2 * | 7/2016 | Kluger ..................... F16F 1/22 |
| 2008/0034883 A1 | 2/2008 | Majeti |
| 2012/0118070 A1 | 5/2012 | Mol et al. |
| 2012/0132467 A1 | 5/2012 | Zeineddine |
| 2015/0233440 A1 * | 8/2015 | Kluger ..................... F16F 1/22 290/1 E |

FOREIGN PATENT DOCUMENTS

| | | |
|---|---|---|
| WO | 2011/066028 A2 | 6/2011 |
| WO | 2011/086427 A1 | 7/2011 |
| WO | 2012/097241 A1 | 7/2012 |

* cited by examiner

STRAIN AMPLIFICATION SENSOR

CROSS-REFERENCE TO RELATED APPLICATIONS

This application claims the benefit of U.S. Provisional Application Nos. 61/970,417, filed on Mar. 26, 2014, and 62/063,449, filed on Oct. 14, 2014. The entire disclosures of each of the above applications are incorporated herein by reference.

GOVERNMENT INTEREST

This invention was made with government support under N00014-13-1-525 awarded by the Navy/Office of Naval Research. The Government has certain rights in the invention.

FIELD

The present disclosure relates to sensors and, more particularly, relates to passive strain sensors and strain amplification sensor.

BACKGROUND AND SUMMARY

This section provides background information related to the present disclosure which is not necessarily prior art. This section provides a general summary of the disclosure, and is not a comprehensive disclosure of its full scope or all of its features.

Passive Strain Sensor 10s are capable of recording strain without any data or power cable tether and can be manufactured and deployed for a fraction of the cost of alternative strain gauges. Commercially available strain gauges have significant limitations when used to monitor a marine structure.

The most common strain gauge uses piezo-electric circuits applied to the material in consideration. To support these circuits, the sensor requires power and data cables which pass changes in resistance through to an amplifier that, using a transfer function, provides the experienced strain. These sensors provide real time strain information and sample on the order of kilohertz. Other monitoring methods employ variations of this conventional piezo-electric strain gauge.

Application of energy harvesting techniques and wireless data transmission allows strain gauges to be deployed without a power or data cable. Both of these options have limitations. Energy harvesting techniques heavily rely on solar energy for implementation on civil structures. Many locations on structures and infrastructures do not, however, provide direct sunlight. There are strain gauges which claim to be operable solely using energy harvested from the structure they are monitoring through capturing the energy associated with strain. These sensors have been shown to be unreliable; if the material does not experience significant strain for an extended period of time the sensor will deplete its stored energy and cease to function.

Additionally, the complexity of these sensors makes them quite costly. Data transmission has been achieved using cellular networks and local wireless networks. Sensors have been deployed on marine structures with wireless data transmission using local networks; however, without strain energy harvesting, these sensors still require a power cable. In the case of marine applications, an additional wireless signal onboard a military vessel is unwelcome and it is difficult to justify wireless implementation of data transfer when a power cable will already be required at every monitoring location—considering it is possible to simply bundle the data and power cable with negligible additional volume. Thus, leading back to the conventional piezo-electric strain sensor as the most viable option, which requires a central amplifier, and power and data transmission cables. Conventional strain sensing systems require tens of thousands of dollars per sensor to implement on civil structures where the monitoring locations are easily accessible.

The alternative strain sensors provided herein can record the experienced strain without requiring a power or data cable, or energy harvesting technique. In some embodiments, these alternative strain sensors are capable of being 3D printed, laser cut, CNC'd, or manufactured using conventional techniques and thus can be manufactured for a fraction of the cost of all alternative sensing methods.

The sensors are capable of recording maximum strain from tensile and compressive loads and can be extended to do so in multiple directions, a limitation of all other available sensing options.

Conventional strain gauges provide a wealth of data that needs to be interpreted to yield relevant information to decision makers. Presently, structural health monitoring (SHM) researchers are swimming in a sea of data producing little information. This is largely because the strain gauges and other sensors provide data that needs to be condensed, stored, and analyzed by methods such as rain flow counting which removes time history indexing in order to make the large amount of data manageable and ultimately interpretable. Analyzing the plethora of data produced by strain sensors is tedious and much of the data is superfluous. Ultimately, using this data to produce relevant and accurate structural health information for decisions is difficult.

Research is being conducted using Bayesian networks (BN) and other modeling techniques to update design-stage engineering assumptions to more closely match the current condition of a structure. Information provided to the BN in the present model is minimal in comparison with many of the SHM updating schemes. The network is presently only updated with information observed from physical inspections such as fatigue crack initiation and permanent set and has shown promising updating power. Additional updating power can be achieved by providing the network with the stress experienced at relevant encoded fatigue-prone details. It is expected that the addition of this data imposed as evidence to the network would increase its prognosis accuracy for structural health and reliability. Extending a BN capable of accurate structural reliability prognosis to a decision support tool would be the next step. This could provide decision makers with accurate, structural health information necessary to make decisions related to the structure's safety and reliability.

In some embodiments, the sensor system of the present teachings can comprise an additional appendage or component can be used to record the maximum experienced strain. In some embodiments, multi-axial strain measurement can be obtained using the same device through additional lever systems. These embodiments, like the aforementioned embodiments, can record strain measurements as a stand-alone unit without requiring a power or data cable, or energy harvesting technique. Furthermore, the sensor can be fabricated using additive manufacturing techniques and thus can be made for a fraction of the cost of all alternative sensing methods.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
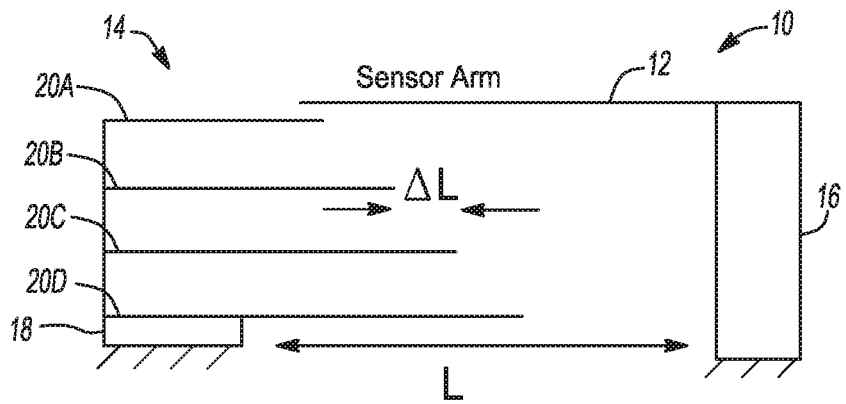
FIG. 1 is a schematic illustrating the principles of the present teachings in some embodiments of the present teachings.

Example embodiments will now be described more fully with reference to the accompanying drawings.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Passive Strain Sensor Overview

According to the principles of the present teachings, in some embodiments, a Passive Strain Sensor 10 (PSS) 10 is provided that employs mechanical methods to record strain. Generally, as schematically illustrated in FIG. 1, the Passive Strain Sensor 10 records maximum strain through a sensor arm 12 progressing down a step-like geometry 14 as strain is imposed between the sensor arm's mounted location 16 and the pyramid 18; both points being fixed to the surface of the material for which strain is being measured.

The Passive Strain Sensor 10 operates off of basic physical properties. When the length between the two fixed elements 16, 18 increases large enough such that the sensor arm 12 is free to fall to the next shelf or step 20A, 20B, 20C, 20D, the pretension in the sensor arm 12 forces it to do so; the resting position of the sensor arm providing no internal stress is resting on the lowest step. Thus, the maximum deflection is recorded by the location of the sensor arm's position on the steps. It is possible to digitally record the maximum strain through a variety of possible configurations of electrodes placed on the sensor arm 12 and step components providing varying resistance depending on the arm location or closing of circuits. The configuration displayed only records the maximum strain due to tensile loads;

however, simply mirroring the steps and sensor arm would provide recording of maximum tensile and compressive strain.

Given the maximum change in length and the initial distance between the two points fixed to the material, using Equations 1-3 we can find the maximum stress experienced in the material. This information can then be provided to the Bayesian Network to predict fatigue life.

$$\in_{max} = \Delta L_{max}/L \quad (1)$$

$$\in_{max} = \sigma_{max}/E \quad (2)$$

$$\sigma_{max} = [E \cdot \Delta L_{max}]/L \quad (3)$$

The fidelity of the sensor can be increased through lengthening the sensor. Fidelity and sensor length are inversely proportional as demonstrated by Equation 3.

Technology

Passive Strain Sensor 10 can be manufactured via additive manufacturing techniques, laser cutting, CNC, or conventional manufacturing techniques. However, Passive Strain Sensor 10 do not require a power source, do not rely on energy harvesting, data acquisition system or associated tether, and is therefore simple to install and monitor and provides strain information orders of magnitude cheaper than alternative systems.

Strain Amplification Sensor

In some embodiments, as illustrated in FIGS. 2-7, by changing the stairs/steps 20A-20D on the Passive Strain Sensor 10 to a lever amplification mechanism, strain can be amplified to be visibly recorded with greater resolution for both tension and compression. A Strain Amplification Sensor (SAS) 50, like the Passive Strain Sensor 10, can record strain measurements as a standalone unit without requiring a power or data cable, or energy harvesting technique as explained herein. This alternative strain sensor can also be fabricated using additive manufacturing techniques, laser cutting, CNC, or conventional techniques and thus can be made for a fraction of the cost of all alternative sensing methods.

SAS Technical Overview

As illustrated in FIGS. 2-7, in some embodiments, Strain Amplification Sensor 50 is an assembly utilizing mechanical methods to record strain. The Strain Amplification Sensor 50 measures and/or records strain in both tension and compression through a sensor arm 52 activating a series of three amplifying members or lever arms 54, 56, 58. It should be understood that although the present teachings will discuss the use of three amplifying members, additional amplifying members can be used. The attachment location of the second lever arm 56 to the third and final lever arm 58 induces opposing relative motion between the second lever arm 56 and the third lever arm 58. In some embodiments, this interaction further improves amplification by providing a total amplification of over 60 times that which is experienced making it possible for visual recording.

Figure 2:
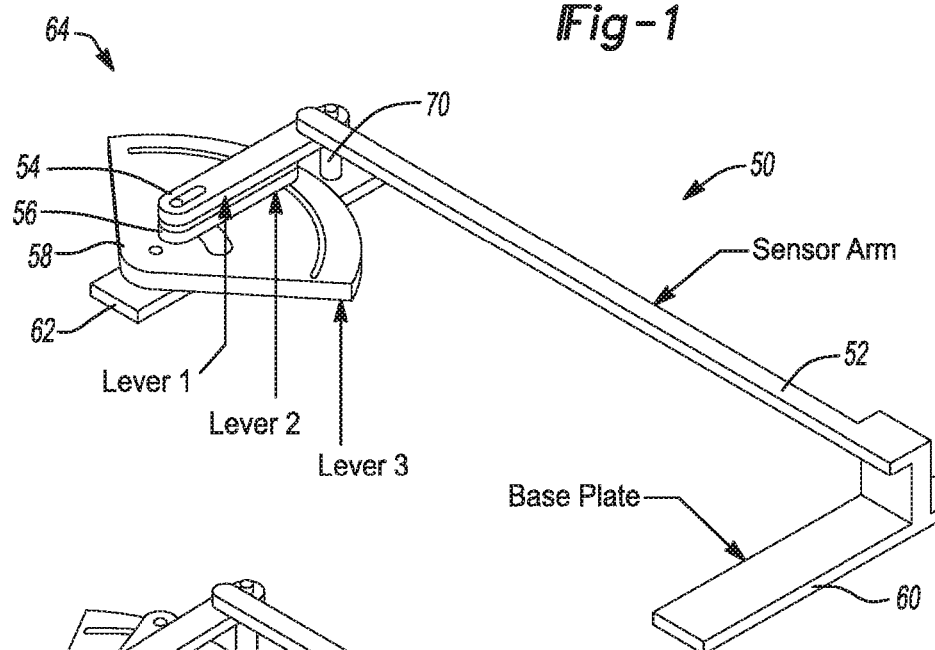
FIG. 2 is a perspective view of a strain amplification sensor according to some embodiments of the present teachings.

Still referring to FIG. 2, Strain Amplification Sensor 50 is illustrated as being secured to the material being measured by adhesion of the two base plates 60, 62 perpendicular to long sensor arm beam 52 connecting the two sides 60, 62. The left hand side contains the amplifying lever system 64 and the right hand side simply provides a fixture for inducing relative motion on the device 10 from the material being measured.

Figure 3:
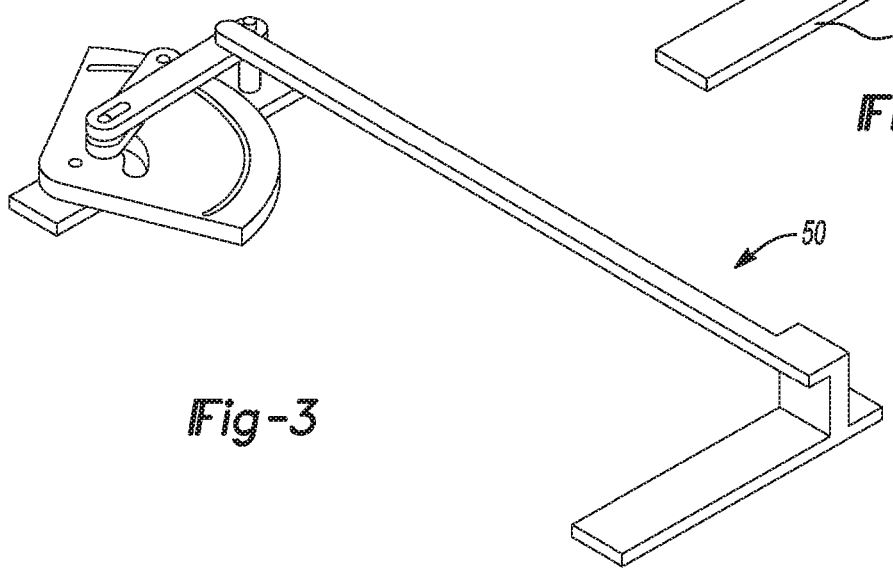
FIG. 3 is a perspective view of the strain amplification sensor of FIG. 2 while under deflection.

As the distance between the two base plates increases or decreases, the lever amplification system is activated. FIG. 3 illustrates the lever system 64 reaction to an increased distance between the two base plates 60, 62. The second lever arm 56 moves away from the system while the third lever arm 58 moves towards the system. Strain is recorded by the location of the end of second lever arm 56 on an arcuate slot 94 of third lever arm 58. Recording the location of the relative motion of these two arms over the slot can be accomplished by fixing either a writing utensil or permanent magnet to the end of the second arm 56. The writing utensil for visual inspection by marking the third arm 58, which may also serve as a method of time history recording. Optical recording is also possible by observing the motions of the pointer on the measurement face over time. This would provide a time history of experienced strain.

Figure 4:
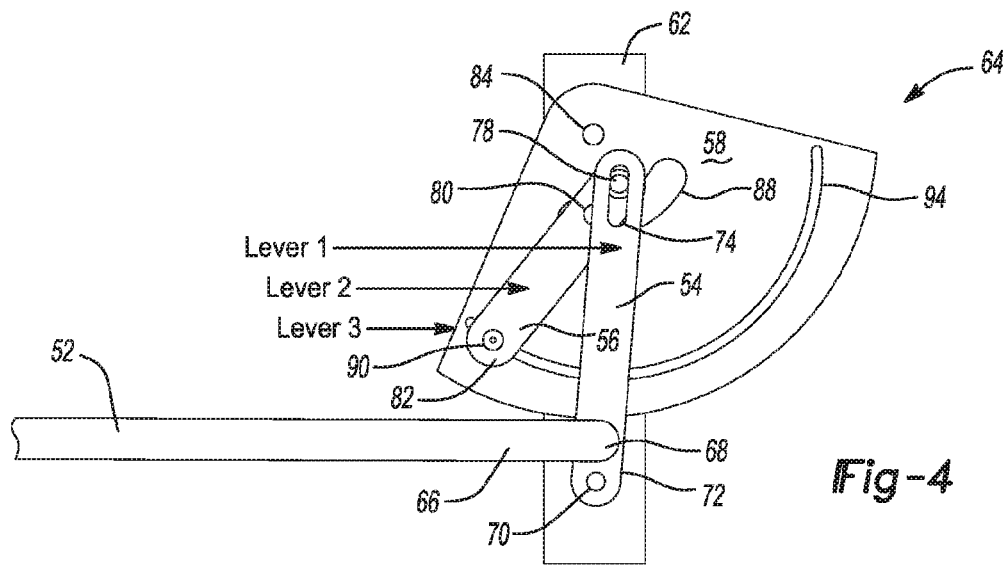
FIG. 4 is an enlarged plan view of the strain amplification sensor of FIG. 2 while under deflection.
Figure 5:
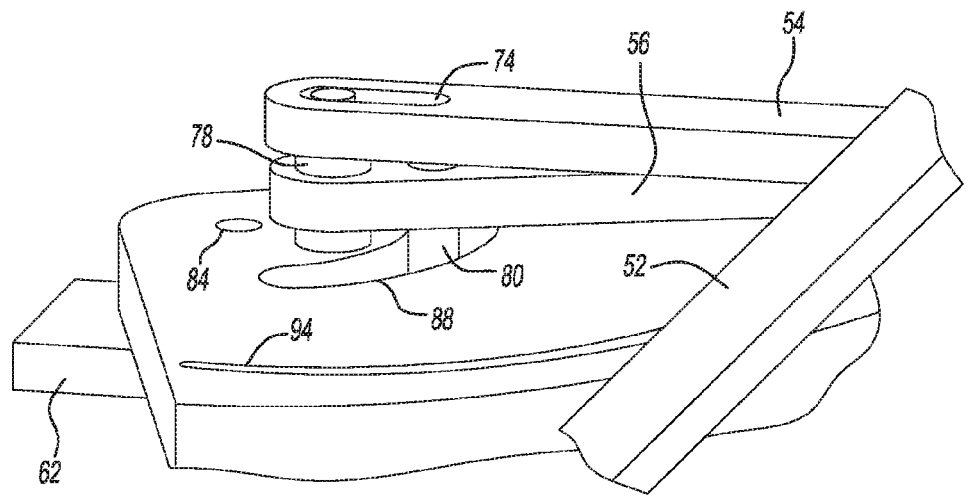
FIG. 5 is an enlarged perspective view of the strain amplification sensor of FIG. 2 while under deflection.
Figure 8:
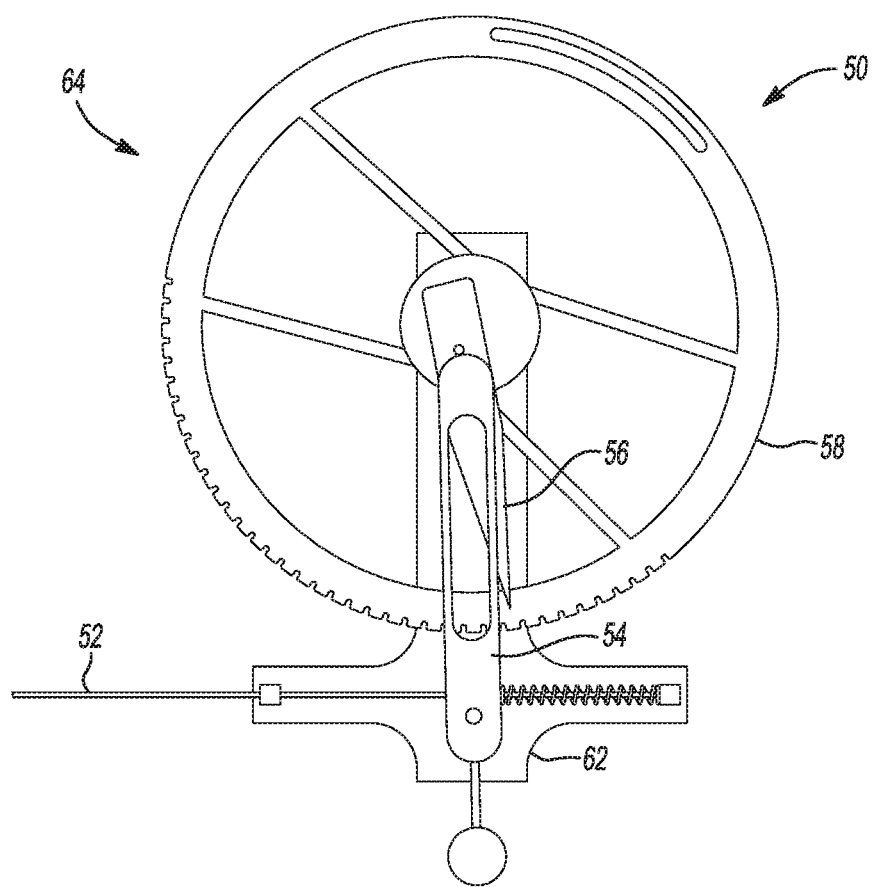
FIG. 8 is a plan view of a strain amplification sensor according to some embodiments of the present teachings.

With reference to FIGS. 4 and 5, additional detail of amplifying lever system 64 is illustrated. As can be seen, in some embodiments, sensor arm 52 is pivotally coupled at end 66 to first lever arm 54 via a pivot 68. As illustrated in FIG. 8, sensor arm 52 may be rigid or a line held in tension by a restoring spring mounted to base plate 62 via another pin. This allows for measurement of displacement between two points in both tension and compression. The tensioned line is rigidly mounted to the material being measured akin to rigid sensor arm 52. It should also be noted in FIG. 8 that third lever arm 58 may be formed as a complete circular member for enhanced balance of third lever arm 58 and to provide improved balancing of first lever arm 54. First lever arm 54 is pivotally coupled to base plate 62 via a pivot 70 (see FIG. 2) at a first end 72. First lever arm 54 further comprises a cam slot 74 extending longitudinally along first lever arm 54. Cam slot 74 is disposed at an opposing end 76. A cam 78 is received within cam slot 74 for camming motion therein. Cam 78 is further fixedly coupled to an end of second lever arm 56 and third lever arm 58 (see FIG. 4). It is also possible to reverse the configuration such that first lever arm 54 comprises a downward facing pin in place of cam slot 74 and lever 56 receives the pin in a slot on the top of the face.

Second lever arm 56 is pivotally coupled to base plate 62 via a pivot 80. In this way, second lever arm 56 is operable to pivot about pivot 80 in response to application of force from first lever arm 54 through the rotation of first lever arm 54 about pivot 70 in response to sensor arm 52. This causes cam 78 to cam along cam slot 74, thereby exerting a force on second lever arm 56. Cam 78 is positioned near pivot 80, thereby causing an increased or exaggerated deflection of opposing end 82 of second lever arm 56.

Similarly, third lever arm 58 is operable to pivot about pivot 84 in response to application of force from first lever arm 54 through the rotation of first lever arm 54 about pivot 70. This causes cam 78 to cam along cam slot 74, thereby exerting a force on third lever arm 56. Cam 78 is positioned near pivot 84, thereby causing an increased or exaggerated deflection of opposing end 86 of third lever arm 58. Third lever arm 58 can comprise an arcuate slot 88 to receive pivot 80 therethrough to permit free articulation of third lever arm 58 about pivot 84.

Figure 6:
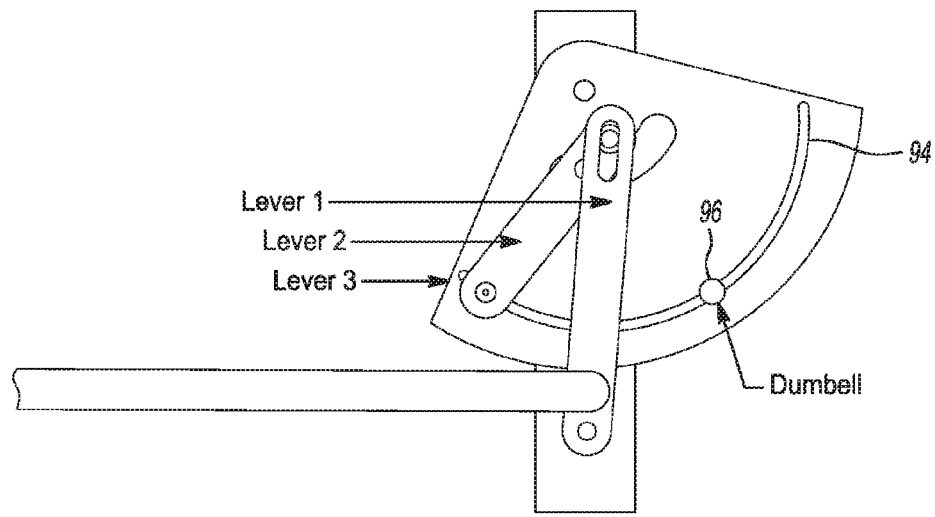
FIG. 6 is a plan view of a strain amplification sensor according to some embodiments of the present teachings.

Furthermore, second lever arm 56 can comprise a pin 90 extending from opposing end 82 that can be slidingly or cammingly received within slot 94 of third lever arm 58. In some embodiments, as illustrated in FIG. 6, slot 94 can comprise a dumbbell or other marker 96 that can be used to mark a location or an extreme deflection of second lever arm 56 relative to third lever arm 58 for recordation of strain. That is, in some embodiments, an incremented place holder can be pushed along slot 94 to record the maximum experienced strain. There are a variety of methods that can be employed to secure the dumbbell or other place holder on the track but a sine wave on both sides along the slot, top and bottom, would provide securement at increments along the slot. Multiple dumbbells can be used of various sizes can be used to record tensile and compressive strain. Dumbbells can vary in size to allow the second lever 56 to pass over in the event of tensile to compressive strain and vice versa. Pin 90 may also be a writing utensil marking the face of the third lever arm 58. Marking thickness and darkness can be used to determine number and distance of passage of pin 90 over lever 58 providing strain time history recording. A thin film or other recording media may be placed over slot 94 and a sharp utensil as pin 90. As the sharp utensil passes over the film or recording media, the increasing length of the created tear can record strain time history.

Greater amplification can be achieved through addition or dimensional changes of lever arms in the amplification mechanism in a configuration similar to the first and second lever arms.

In some embodiments, the Strain Amplification Sensor 50 is a 3D printed, plastic assembly with only mechanical methods to record strain. The Strain Amplification Sensor 50 records strain in both tension and compression through a sensor arm activating amplifying lever system 64. The attachment location of the second lever arm 56 to the third and final lever arm 58 induces opposing relative motion between the second lever arm 56 and the third 58. This interaction further improves amplification providing a total amplification, in some embodiments, of over 60 times that which is experienced making it possible for visual recording. However, it should be understood that the magnitude of amplification is dependent upon the dimensions and pivot locations of the lever arms which can be varied as desired for the particular application.

Third lever arm 58 is not limited to the pie shape as depicted. A circular shape provides balance for decreased internal friction for varying mounting orientations. Similarly, lever arms 54 and 56 are not limited to bars; they too can be designed with varying shapes for balance to reduce internal friction realized from non-vertical mounting orientations.

Figure 7:
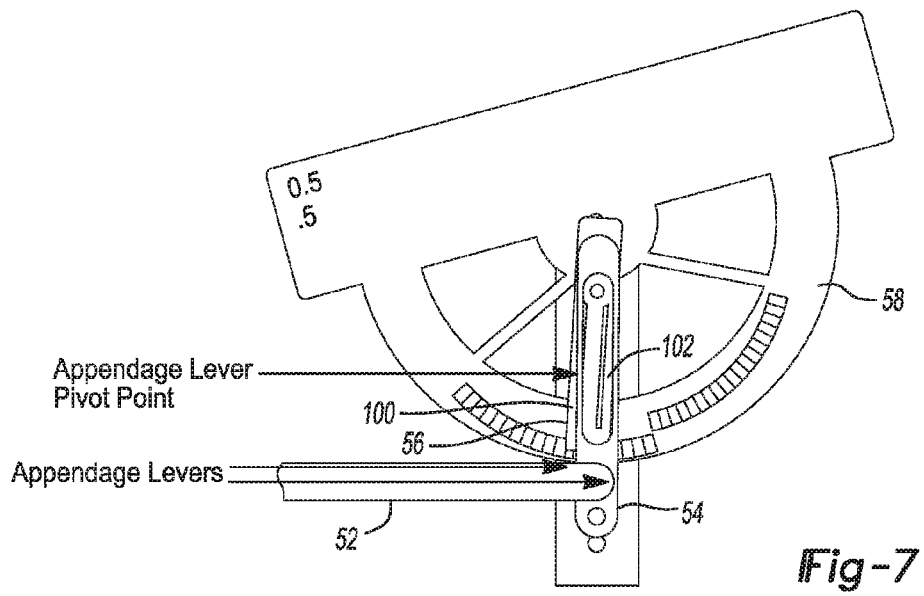
FIG. 7 is a perspective view of a strain amplification sensor according to some embodiments of the present teachings.

As seen in FIG. 7, modification of the second lever arm 56 with the addition of two lever appendages 100, 102 that pivot about either side of the second lever arm 56 provides the ability to record the maximum experienced strain. Coupled with the addition of a series of sawtooth teeth 104 on third lever member 58 (see FIG. 7), the two appendage levers are pushed along the tooth tracks. The higher the strain the greater the distance the appendage arm moves up the track and stays. Lever two is free to re-center and the appendage levers will remain fixed to the point of maximum strain.

Multi-axial strain can be recorded with one strain amplification sensor by placing additional base plates along the desired axes. Layering the equivalent number of sets of levers 1, 2, and 3 for each base plate provides a compact display of experienced strain along the axes on which the base plates are adhered. Multiple layers of lever sets can be achieved by extending the pivot pins and placing spacers between each set. Offsetting the resting location of lever 1 and lever 3 for each layer aids in visual observation of each axis of strain when viewed from the top. The maximum strain value and time history recording features discussed above can be implemented on each of these lever sets.

The present teachings may find utility in a wide variety of applications, including monitoring structural health of any one of the following industry sectors: manufacturing—quality control processes; material testing processes; marine—commercial ships, naval vessels, offshore oil and gas rigs; civil—bridges, buildings, and infrastructure; and aerospace—commercial and military.

The present teachings further provide a number of advantage over conventional solutions including, but not limited to, orders of magnitude cheaper than the cost of conventional system, no power supply necessary, does not rely on captured energy, and data acquisition system and tether are unnecessary.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A passive strain sensor comprising:
   a first portion being coupled to a first member to be strain measured;
   a second portion being coupled to a second member to be strain measured;
   at least one arm extending from at said first portion and movable therewith; and
   a plurality of step members extending from said second portion, each of said plurality of step members having a different length such that strain between said first portion and said second portion causes said at least one arm to move from one of said plurality of step members to a second of said plurality of step members thereby indicating a magnitude of strain.

2. A strain amplification sensor comprising:
   a first portion being coupled to a first member to be strain measured;
   a second portion being coupled to a second member to be strain measured; and
   a multi-arm system pivotally coupled between said first portion and said second portion, an attachment location of said multi-arm system induces opposing relative motion resulting in detectable deflection of said multi-arm system in response to application of strain between said first portion and said second portion.

3. The strain amplification sensor according to claim 2 wherein said multi-arm system comprises:
   a sensor arm extending from said first portion and movable therewith;
   a first lever arm pivotally coupled to said sensor arm and pivotable in response to movement of said sensor arm about a first pivot, said first lever arm being pivotally coupled to said second portion via said first pivot;
   a second lever arm pivotally coupled to said first lever arm at a first end of said second lever arm and pivotable in response to movement of said first lever arm about a second pivot, said second lever arm being pivotally coupled to said second portion via said second pivot; and
   a third lever arm pivotally coupled to said first lever arm and pivotable in response to movement of said first lever arm.

4. The strain amplification sensor according to claim 3 wherein said first lever arm comprises a cam slot, said cam slot receiving a cam extending from said second lever arm.

5. The strain amplification sensor according to claim 3 wherein said second lever arm is pivotally coupled to said first lever arm at said first end at a location relative to said second pivot to result in greater translation of an opposing end of said second lever arm.

6. The strain amplification sensor according to claim 3 wherein an opposing second end of said second lever arm is received within an arcuate slot formed in said third lever arm, a relative position of said second lever arm and said third lever arm providing said detectable deflection of said multi-arm system in response to application of strain between said first portion and said second portion.

7. The strain amplification sensor according to claim 6, further comprising a marker disposed within said arcuate slot.

8. The strain amplification sensor according to claim 3, further comprising:
   at least one appendage lever extending from said second lever arm for recording said strain.

9. The strain amplification sensor according to claim 2, further comprising:
   a system for recording a maximum experienced strain.

10. The strain amplification sensor according to claim 2, further comprising:
    a system for recording strain time history.

11. The strain amplification sensor according to claim 2 wherein said detectable deflection is visually detectable.

12. The strain amplification sensor according to claim 2 wherein said detectable deflection is electrically detectable.

13. The strain amplification sensor according to claim 2 wherein said detectable deflection is recorded using relative motion of said multi-arm system to propagate a crack or tear.

14. A strain amplification sensor comprising:
    a first base portion being coupled to a first member to be strain measured;
    a second base portion being coupled to a second member to be strain measured; and
    an amplifying lever system pivotally coupled between said first base portion and said second base portion, attachment locations of said amplifying lever system induces opposing relative motion resulting in detectable deflection of said amplifying lever system in response to application of strain between said first base portion and said second base portion, said amplifying lever system having:
    a sensor arm extending from said first base portion and movable therewith;
    a first lever member pivotally coupled to said sensor arm and pivotable in response to movement of said sensor arm about a first pivot, said first lever member being pivotally coupled to said second base portion via said first pivot;
    a second lever member pivotally coupled to said first lever member at a first end of said second lever member and pivotable in response to movement of said first lever member about a second pivot, said second lever member being pivotally coupled to said second base portion via said second pivot; and
    a third lever member pivotally coupled to said first lever member and pivotable in response to movement of said first lever member.

15. The strain amplification sensor according to claim 14 wherein said first lever member comprises a cam slot, said cam slot receiving a cam extending from said second lever member.

16. The strain amplification sensor according to claim 14 wherein said second lever member is pivotally coupled to said first lever member at said first end at a location relative to said second pivot to result in greater translation of an opposing end of said second lever member.

17. The strain amplification sensor according to claim 14 wherein an opposing second end of said second lever member is received within an arcuate slot formed in said third lever member, a relative position of said second lever member and said third lever member providing said detectable deflection of said multi-arm system in response to application of strain between said first base portion and said second base portion.

18. The strain amplification sensor according to claim 15, further comprising a marker disposed within said arcuate slot.

19. The strain amplification sensor according to claim 14, further comprising:
    at least one appendage lever extending from said second lever member for recording said strain.

20. The strain amplification sensor according to claim 14, further comprising:
    a system for recording a maximum experienced strain.

* * * * *

UNITED STATES PATENT AND TRADEMARK OFFICE
CERTIFICATE OF CORRECTION

| | | |
|---|---|---|
| PATENT NO. | : 9,546,917 B2 | Page 1 of 1 |
| APPLICATION NO. | : 14/669139 | |
| DATED | : January 17, 2017 | |
| INVENTOR(S) | : Mark D. Groden et al. | |

It is certified that error appears in the above-identified patent and that said Letters Patent is hereby corrected as shown below:

Column 10, Claim 16, Line 21-25, delete "16. The strain amplification sensor according to claim 14 wherein said second lever member is pivotally coupled to said first lever member at said first end at a location relative to said second pivot to result in greater translation of an opposing end of said second lever member." and insert --16. The strain amplification sensor according to claim 15, further comprising a marker disposed within said arcuate slot.-- therefor Column 10, Claim 17, Line 26-33, delete "17. The strain amplification sensor according to claim 14 wherein an opposing second end of said second lever member is received within an arcuate slot formed in said third lever member, a relative position of said second lever member and said third lever member providing said detectable deflection of said multi-arm system in response to application of strain between said first base portion and said second base portion." and insert --17. The strain amplification sensor according to claim 14 wherein said second lever member is pivotally coupled to said first lever member at said first end at a location relative to said second pivot to result in greater translation of an opposing end of said second lever member.-- therefor Column 10, Claim 18, Line 34-36, delete "18. The strain amplification sensor according to claim 15, further comprising a marker disposed within said arcuate slot." and insert --18. The strain amplification sensor according to claim 14 wherein an opposing second end of said second lever member is received within an arcuate slot formed in said third lever member, a relative position of said second lever member and said third lever member providing said detectable deflection of said multi-arm system in response to application of strain between said first base portion and said second base portion.-- therefor Signed and Sealed this
Fourteenth Day of November, 2017

Joseph Matal
*Performing the Functions and Duties of the
Under Secretary of Commerce for Intellectual Property and
Director of the United States Patent and Trademark Office*